US00PP22780P3

(12) United States Plant Patent
Slaughter et al.

(10) Patent No.: US PP22,780 P3
(45) Date of Patent: Jun. 12, 2012

(54) PEACH TREE NAMED 'BURPEACHTWENTYTHREE'

(50) Latin Name: *Prunus persica*
Varietal Denomination: Burpeachtwentythree

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 263 days.

(21) Appl. No.: 12/590,943

(22) Filed: Nov. 16, 2009

(65) Prior Publication Data

US 2011/0119797 P1 May 19, 2011

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

PP6,025 P * 9/1987 Balakian ..... Plt./198
PP14,627 P3 * 3/2004 Byrne et al. ..... Plt./197

* cited by examiner

*Primary Examiner* — Wendy C Haas
(74) *Attorney, Agent, or Firm* — Paine Hamblen, LLP

(57) ABSTRACT

A new and distinct variety of peach tree (*Prunus persica*), which is denominated varietally as Burpeachtwentythree', and which produces an attractively colored yellow-fleshed, clingstone peach which is mature for harvesting and shipment approximately May 5 to May 10 under the ecological conditions prevailing in the San Joaquin Valley of central California.

1 Drawing Sheet

Botanical designation: *Prunus persica.*
Varietal denomination: 'BURPEACHTWENTYTHREE'.

BACKGROUND OF THE NEW VARIETY

The present invention relates to a new, novel and distinct variety of peach tree, *Prunus persica* and which has been denominated varietally as 'Burpeachtwentythree'.

ORIGIN

The present variety of peach tree resulted from an on-going program of fruit and nut tree breeding. The purpose of this program is to improve the commercial quality of deciduous fruit and nut varieties and rootstocks, by creating and releasing promising selections of *Prunus, Malus* and *Regia* species. To this end we make both controlled and hybrid cross pollinations each year in order to produce seedling populations from which improved progenies are evaluated and selected.

The seedling, 'Burpeachtwentythree' was originated by us and selected from a population of seedlings growing in our experimental orchards located near Fowler, Calif. The seedlings, grown on their own roots, were derived from a cross that we made in 2000 of an unnamed, un-patented, early ripening, yellow-fleshed, clingstone peach tree which was used as the seed parent; and the low-chilling requirement peach tree named 'Tropic Beauty' (Unpatented) which was used as the pollen parent. The seeds from this cross were embryo cultured, in vitro, and then subsequently grown in a greenhouse to an appropriate stage. Subsequently, the new plants were field planted, and grown for further evaluation. One seedling which is the present variety, exhibited especially desirable characteristics, and was designated as 'J40.111'. This seedling was marked for subsequent observation. After the 2001 fruiting season, the new variety of peach tree was selected for advanced evaluation and repropagation.

ASEXUAL REPRODUCTION

Asexual reproduction of this new and distinct variety of peach tree was accomplished by budding the new peach tree to 'Nemaguard' Rootstock (un-patented). This was performed by us in our experimental orchard which is located near Fowler, Calif. in 2002. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachtwentythree' is a new and distinct variety of peach tree, which is considered of relatively large size, and which has vigorous growth. This new peach tree is also a regular and productive bearer of relatively large, firm, yellow-fleshed, clingstone fruit which have good flavor and eating qualities. This new tree has a low chilling requirement of approximately 175 hours, and further produces relatively uniformly sized fruit throughout the tree. In addition to the foregoing, the fruit of the new tree also appears to have good handling and shipping qualities.

The 'Burpeachtwentythree' peach tree bears fruit which are ripe for commercial harvesting and shipment on approximately May 5 to May 10 under the ecological conditions prevailing in the San Joaquin Valley of central California. In relative comparison with the 'Flordaprince' peach tree (Unpatented), the present new variety of peach tree bears fruit which ripen at about the same time but is which is considerably larger when both trees have been grown and evaluated at the same geographical location. In relative comparison to the unnamed peach which was the seed parent, the fruit of the new variety of peach tree ripens about 7 days later. In relative comparison to the peach tree, 'Queencrest' (U.S. Plant Pat. No. 6,025), which is the most similar variety known to the inventors at this time, the new variety produces fruit which ripen at least 4 days or more earlier. Additionally, the 'Burpeachtwentythree' peach tree yields substantially more harvestable fruit than do trees of the 'Queencrest' peach tree variety (U.S. Plant Pat. No. 6,025).

BRIEF DESCRIPTION OF THE DRAWING

The accompanying drawing, which is provided, is a color photograph of the new peach tree variety. The photograph depicts two whole mature fruit, and one mature fruit dissected laterally in the sagittal plane at the basal end, and which reveals the flesh characteristics thereof. The external coloration of the fruit as shown in the photograph is sufficiently matured for harvesting and shipment. Additionally, the photograph displays a sample vegetative shoot bearing typical leaves. Also a typical stone, with the flesh removed to display the appearance of same, has been provided. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates (Royal Horticultural Society, Fourth Edition, 2001) and descriptions provided hereinafter.

DETAILED DESCRIPTION

Referring more specifically to the pomological details of this new and distinct variety of peach tree, the following has been observed during the fifth fruiting season under the ecological conditions prevailing at orchards of the assignee which are located near the town of Fowler, in the county of Fresno, of the state of California. All major color code designations are by reference to The R.H.S. Colour Chart (Fourth Edition, 2001) provided by The Royal Horticultural Society of Great Britain. Common color names are also occasionally used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

TREE

Size: Generally—Considered large as compared to other common commercial peach cultivars ripening in the early season of maturity. The tree of the present variety was pruned to a height of approximately 300.0 cm to about 305.0 cm at maturity.

Vigor: Considered vigorous. The present peach tree variety grew from about 155.0 cm. to about 165.0 cm. in height during the first growing season. The new variety was pruned to a height of approximately 150.0 cm. during the first dormant season, and primary scaffolds were then selected for the desired tree structure.

Productivity: Productive. Fruit set varies from about 2.5 to several times more than the desired crop load. The fruit set is spaced by thinning to develop the remaining fruit into the desired market sized fruit. The number of the fruit set varies with the prevailing climatic conditions, and cultural practices employed during the bloom period, and is therefore not distinctive of the variety.

Bearer: Regular. Fruit set has been heavy during the previous years of observation, and thinning was necessary during the past 5 years on both the original seedling and also on the subsequent propagations.

Form: Upright, and pruned into a vase shape.

Density: Considered dense. It has been discovered that pruning the branches from the center of the tree to obtain a resulting vase shape allows for air movement and appropriate amounts of sunlight to enhance fruit color and renewal of fruiting wood throughout the tree.

Hardiness: The present tree was grown and evaluated in USDA Hardiness Zone 9. Winter chilling requirements of the new tree are approximately 175 hours below 7.0 degrees C. The variety appears to be hardy under typical central San Joaquin Valley climatic conditions. Because of its lower chilling requirement the present variety of tree appears that it could be suitably grown in climates that have fewer chilling hours than that of USDA Hardiness Zone 9.

TRUNK

Diameter: Approximately 14.3 cm. in diameter when measured at a distance of approximately 15.24 cm. above the soil level. This measurement was taken at the end of the fifth growing season.

Bark texture: Considered moderately rough, with numerous folds of papery scarfskin being present.

Lenticels: Generally—Very numerous flat, oval lenticels are present. The lenticels range in size from approximately 4.0 millimeters in width, and about 1.0 millimeter in height. The development and size of the lenticels can be influenced by growing conditions and are therefore not necessarily a dependable descriptor.

Lenticel color: Considered an orange brown, (RHS Greyed-Orange Group N172 D).

Bark coloration: Variable, but it is generally considered to be a medium brown, (RHS Grey-Brown Group N199 C). This bark description was taken from trees in their fifth leaf which have not as yet ruptured the scarf skin nor developed bark furrowing which is more typical of older trees.

BRANCHES

Size: Considered medium for the variety.

Diameter: Average as compared to other peach varieties. The branches have a diameter of about 8.0 centimeters when measured during the fifth year after grafting.

Surface texture: Average, and appearing furrowed on wood which is several years old.

Crotch angles: Primary branches are considered variable, and are between about 50 to about 55 degrees when measured from a horizontal axis. This particular characteristic is not considered distinctive of the variety, however.

Current season shoots:

*Surface texture.*—Substantially glabrous.

Internode length: Approximately 2.4 cm.

Color of mature branches: Grey brown, (RHS Grey-Brown group 199 B).

Current seasons shoots:

*Color.*—Light green, (RHS Yellow-Green Group 144 B). The color of new shoot tips is considered a bright and shiny green (RHS Green Group 141 C).

LEAVES

Size: Considered medium large for the species. Leaf measurements have been taken from vigorous, upright, current-season growth at approximately mid-shoot.

Leaf length: Approximately 157.0 to about 179.0 millimeters.

Leaf width: Approximately 32.0 to about 43.0 millimeters.

Leaf base shape: Considered reasonably uniform in its marginal symmetry relative to the longitudinal axis of the leaf.

Leaf form: Lancelolate.

Leaf tip form: Acuminate.

Leaf color:

*Upper Leaf Surface.*—Dark green, (approximately RHS Green Group 141 B).

Leaf texture: Glabrous.

Leaf color:

*Lower Surface.*—Medium green, (approximately RHS Yellow-Green Group 144 B).

Leaf venation: Pinnately veined.

Mid-vein:

*Color.*—Considered a light yellow-green, (approximately RHS Yellow-Green Group 149 D) in the early to mid period of the growing season.

Leaf margins: Slightly undulating.

*Form.*—Considered finely crenate.

*Uniformity.*—Considered generally uniform.

Leaf petioles:

*Size.*—Considered long.

*Length.*—About 10.0 to about 12.0 mm.

*Diameter.*—About 1.5 to about 2.0 mm.

*Color.*—Pale green, (approximately RHS Yellow-Green Group 144 B).

Leaf glands:

*Size.*—Considered small. Approximately 1.0 mm in length, and about 1.0 mm in height.

*Number.*—Generally, one gland per margin side. Occasionally two glands per margin side.

*Type.*—Generally considered a tight small reniform gland.

*Color.*—Considered a dark tan (RHS Grey-Orange Group 166 C).

Leaf stipules:

*Size.*—Medium large for the variety. Approximately 8-14 mm. in length and 1-2.5 mm. in width. This characteristic is not distinctive of the variety.

*Number.*—Typically 2 per leaf bud, and up to 6 per shoot tip.

*Form.*—Lanceolate in form and having a serrated margin.

*Color.*—Green, (approximately RHS Green Group 141 B) when young, but graduating to a brown color, (approximately RHS Grey-Orange group 174 C) with advancing senescence. The stipules are considered to be early deciduous.

FLOWERS

Flower buds: Generally—Depending upon the stage of development, the flower buds are approximately 7.0 millimeters wide; about 11.0 millimeters long; conic in form; and slightly appressed relative to the bearing shoot.

Flower buds:

*Color.*—This characteristic is dependent upon the proximity to the bloom. The bud scales are deep purple, (approximately RHS Greyed-Purple Group N186 C). The buds are considered hardy under typical central San Joaquin Valley climatic conditions.

Hardiness: No winter injury (bud death) has been noted during the last several years of evaluation in the central San Joaquin Valley. The current variety has not been intentionally subjected to drought or heat stress, and therefore this information is not available. It should be noted that temperatures below freezing can occur during and after the initiation of bloom for this variety and it has exhibited blossom damage during such low-temperature exposures. Care should be taken in latitude and specific site locations where freezing can occur when considering this variety for planting.

Date of first bloom: Observed on Jan. 9, 2008.

Blooming time: Considered early in relative comparison to other commercial peach cultivars grown in the central San Joaquin Valley. The date of full bloom was observed on Jan. 15, 2008. The date of full bloom varies slightly with climatic conditions and prevailing cultural practices.

Duration of bloom: Approximately 8 days. This characteristic varies slightly with the prevailing climatic conditions.

Flower type: The variety is considered to have a showy type flower.

Flower size: The flower diameter at full bloom is approximately 44.0 to about 53.0 millimeters.

Bloom quantity: Considered abundant.

Flower bud frequency: Normally 2 flower buds appear per node, occasionally one, rarely more than 2.

Petal size: Generally—Considered medium for the species.

*Length.*—Approximately 21.0 to about 24.0 millimeters.

*Width.*—Approximately 18.0 to about 21.0 millimeters.

Petal form: Considered ovate.

Petal count: Nearly always 5.

Petal texture: Glabrous.

Petal color: Light pink, (approximately RHS Red-Purple Group 65 C) to a medium pink, (approximately RHS Red-Purple Group 65 A).

Fragrance: Slight.

Petal claw:

*Form.*—The claw is considered generally ovoid, and has a medium size when compared to other varieties.

*Length.*—Approximately 7.0 to about 11.0 millimeters.

*Width.*—Approximately 6.0 to about 9.0 millimeters.

Petal margins: Generally considered variable, from nearly smooth to slightly ruffled, and moderately undulate to ruffled.

Petal apex: Generally—The petal apices generally appear entire at the tip.

Flower pedicel:

*Length*.—Considered medium-long, and having an average length of approximately 5.0 to about 6.0 millimeters.

*Diameter*.—Considered average, approximately 3.0 millimeters.

*Color*.—A medium brown, (approximately RHS Grey-Brown Group N199 C).

Floral nectaries:

*Color*.—A dull orange, (approximately RHS Grey-Orange Group N172 D).

Calyx:

*Surface Texture*.—Generally glabrous.

*Color*.—A dull purple, (approximately RHS Grey-Purple Group 187 C).

Sepals:

*Surface Texture*.—The surface of the sepals have a short, fine pubescent texture.

*Size*.—Average, and ovate in form.

*Color*.—A dull red, (approximately RHS Grey-Red Group 182 B).

Anthers: Generally—Average in length.

*Color*.—A bright golden yellow, (approximately RHS Yellow Group 9 C).

Pollen production: Pollen is abundant, and has a yellow color, (approximately RHS Yellow-Orange Group 17 B).

Fertility: No pollinator is required.

Filaments:

*Size*.—Length is variable, approximately 12.0 to about 15.0 millimeters long.

*Color*.—Considered white at observation time, but turns to a light pink with increasing age, (approximately RHS Red Group 55 D).

Pistil:

*Number*.—Usually 1, and occasionally 2, rarely more than 2.

*Generally*.—Average in size.

*Length*.—Approximately 17.0 to about 19.0 millimeters including the ovary.

*Color*.—Considered a very pale green, (approximately RHS Yellow-Green Group 145 C).

*Surface texture*.—The variety has a long pubescent pistil.

FRUIT

Maturity when described: Firm ripe condition (shipping ripe).

Date of first picking: May 5, 2008.

*Date of last picking*.—May 15, 2008. The date of harvest varies slightly with the prevailing climatic conditions.

Size: Generally—Considered large, and uniform.

Average cheek diameter: Approximately 63.0 to about 70.0 millimeters.

Average axial diameter: Approximately 64.0 to about 69.0 millimeters.

Typical weight: Approximately 190.0 grams. This characteristic is highly dependent upon the prevailing cultural practices, and therefore is not particularly distinctive of the variety.

Fruit form: Generally—Considered rounded. The fruit is generally uniform in symmetry. It should be noted that occasional asymmetry can occur in the axial hemispheres of the fruit.

Fruit suture: Very shallow and appearing almost non-indented. The fruit suture extends from the base to the apex. Slight grooving is typically observed toward the apex. No apparent callousing or stitching exists along the suture line.

Suture:

*Color*.—Generally, blushed to the same degree as the skin, (approximately RHS Red Group 46 B).

Ventral surface:

*Form*.—Only slightly indented.

Apex: Rounded.

Base: Gently retuse.

Stem cavity: Generally rounded and uniform. Average depth of the stem cavity is about 5.0 mm. Average width of the stem cavity is about 10 mm.

Fruit skin:

*Thickness*.—Considered medium in thickness, and tenacious to the flesh.

*Texture*.—Short, fine and pubescent. The pubescence is moderately abundant.

*Taste*.—Non-astringent.

*Tendency to crack*.—None observed in the previous years of evaluation in the Southern San Joaquin Valley.

Color:

*Blush color*.—Generally speaking, a red blush exists on a majority of the skin of the fruit (approximately RHS Red Group 46 B), and is typically more present on the basal portion of the fruit. The blush covers approximately 70-80% of the fruit skin surface. The percentage of the blush on the fruit skin surface can vary, and is generally dependent upon the fruit's exposure to sunlight, specific fruit maturity and also the prevailing ecological and cultural conditions under which the fruit was grown.

*Ground Color*.—Yellow, (approximately RHS Yellow-Orange Group 19 B). The ground color of the fruit can vary significantly by the maturity of the fruit when this measurement is taken. In particular, when the fruit is less mature, the ground color will appear yellow-green (RHS Group 150D). However, with greater maturity, the ground color will appear more yellow-gold (RHS Group 19B).

Fruit stem: Medium in length, approximately 6.0 to about 8.0 millimeters.

*Diameter*.—Approximately 2.0 to about 3.0 millimeters.

*Color*.—Pale yellow-green, (approximately RHS Yellow-Green Group N144D).

Flesh:

*Ripening*.—Considered even.

*Flesh texture*.—Firm, juicy and dense. Considered non-melting.

*Flesh fibers*.—Few are found.

*Flesh aroma*.—Very slight.

*Eating quality*.—Considered very good.

*Flesh flavor*.—Considered sweet and mildly acidic. The flavor is considered both pleasant and balanced. According to palate and smell observations, there is no distinguishable amygdalin in the flesh.

*Juice production*.—Moderate.

*Brix*.—About 10.0 to 14.0 degrees. This characteristic varies slightly with the number of fruit per tree; maturity of fruit when harvested, prevailing cultural practices; and the surrounding climatic conditions.

*Flesh color*.—Pale yellow-orange, (approximately RHS Yellow-Orange Group 20 C).

STONE

Type: Clingstone.

Size: Considered medium-large for the variety. The stone size varies significantly depending upon the tree vigor, crop load and the prevailing growing conditions.

Length: Average, about 27.0 to about 31.0 millimeters.

Width: Average, about 22.0 to about 25.0 millimeters.

Diameter: Average, about 15.0 to about 18.0 millimeters.

Form: Ovoid.

Base: The stone is usually rounded and considered narrow or slightly elongated relative to the general shape.

Apex:

*Shape*.—The stone apex is slightly lobed, and generally without a prominent apical tip.

Stone surface:

*Surface texture*.—Generally speaking, in view of the early ripening nature of the present variety, the stone of the present variety normally does not have sufficient time to develop and mature when compared to the stones of medium or later ripening varieties. Additionally, because lignification has just begun to occur when the present variety has ripened, few dependable descriptors can be assigned to the stones characteristics. Surface pitting is generally more noted along each of the lateral sides of the stone. Larger pits are generally noted nearer the stone apex and smaller pits are generally found nearer the stone base.

*Ridges*.—Ridging is generally more prominent when viewed from a location which is parallel and lateral relative to the suture line. In view of the early ripening nature of the present variety, the stone normally does not have sufficient time to fully develop and mature when compared to the stone produced by medium or later ripening varieties. Additionally, because lignification has just begun to occur when the present variety has ripened, few dependable descriptors can be assigned to the characteristics of the stone.

*Ventral edge*.—The ventral edge is generally considered moderately smooth with even labia bracketing the ventral suture.

*Dorsal edge*.—Shape — Generally considered moderately rough, and uneven. Folds of surface ridges on the external margins often end abruptly along the external margin of the dorsal surface creating an irregular edge.

Stone color: The color of the dry stone is generally considered a pale yellow white, (approximately Yellow Group RHS 11 D). This color depends, at least in part, on the moisture content of the stone. Further, the stone color may vary because of oxidation. In view of this color variability, this characteristic cannot be considered distinctive of the present variety.

Tendency to split: Splitting has occasionally been noted.

Kernel size: The kernel is considered medium-small.

*Kernel form*.—Considered generally ovoid but as the immature embryo and its cotyledons have not fully developed, the kernel form is generally considered shriveled and underdeveloped especially on the basal end.

Pellicle: Slightly pubescent.

Color: (RHS Yellow-Orange Group 19 D).

Use: The subject variety 'Burpeachtwentythree' is considered to be an early season peach tree which produces fruit which are considered to be firm, attractively colored, and which are useful for both local and long distance shipping.

Fruit keeping quality: Appears excellent. Fruit has stored well up to 30 days after harvest at 1.0 degree Celsius.

Fruit shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control, frost, climatic variables and horticultural management are to be expected.

Having thus described and illustrated our new variety peach tree, what we claim is new and desire to secure by Plant Letters Patent is:

1. A new distinct variety of peach tree, substantially as illustrated and described, and which is characterized principally as to novelty by producing an attractively colored yellow-fleshed, clingstone peach which is mature for harvesting and shipment approximately May 5 to May 10 under the ecological conditions prevailing in the San Joaquin Valley of central California.

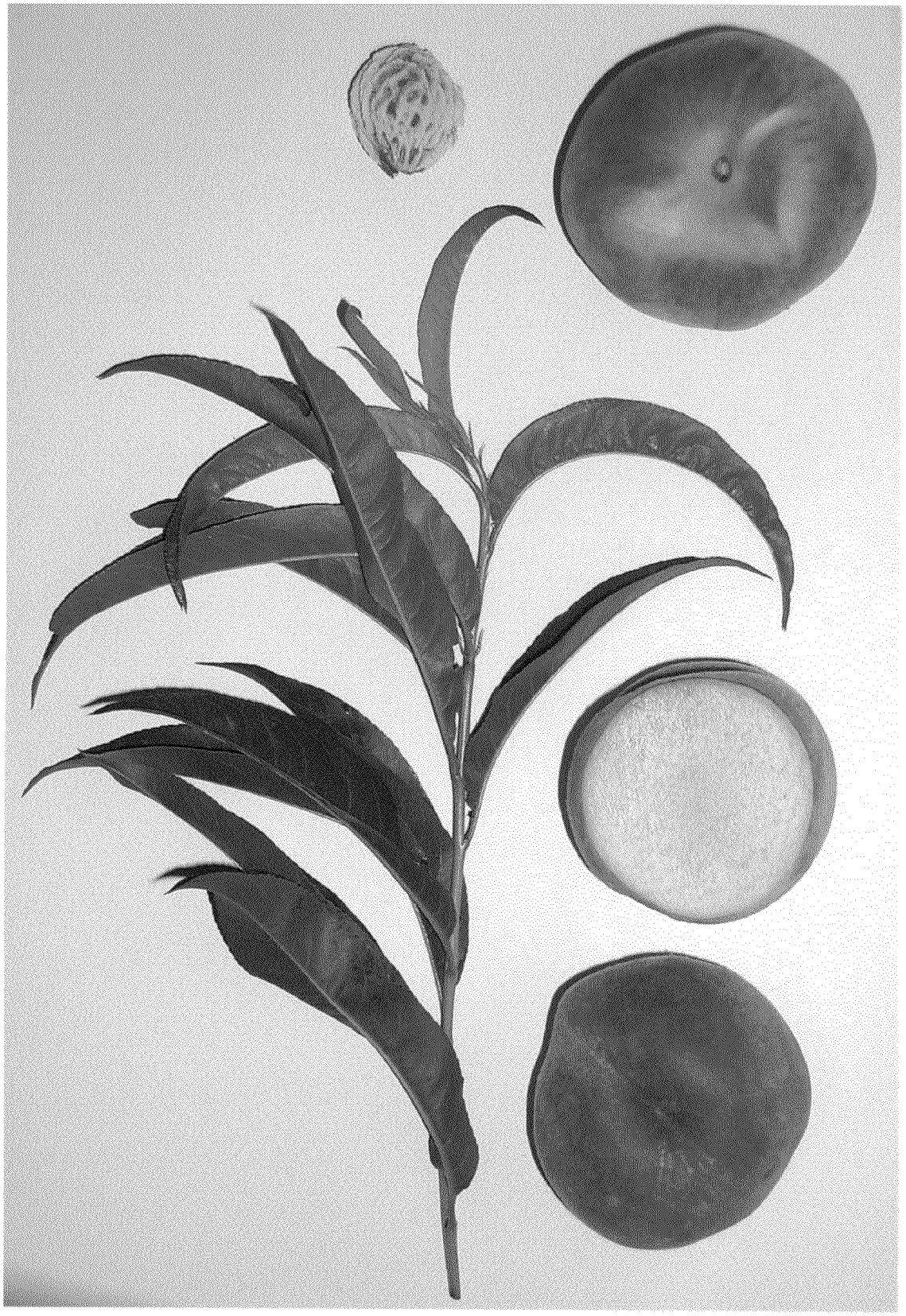

* * * * *